United States Patent [19]

Takematsu et al.

[11] Patent Number: 4,579,969

[45] Date of Patent: Apr. 1, 1986

[54] SUBSTITUTED 1,3-DIBENZYLUREAS AND HERBICIDAL COMPOSITIONS CONTAINING THEM

[75] Inventors: Tetsuo Takematsu; Yasutomo Takeuchi, both of Utsunomiya; Michiyuki Kohno, Maebashi; Akihiko Aoki, Tochigi; Koichi Moriya, Shibukawa, all of Japan

[73] Assignee: The Japan Carlit Co., Ltd., Tokyo, Japan

[21] Appl. No.: 687,131

[22] Filed: Dec. 28, 1984

[30] Foreign Application Priority Data

Feb. 20, 1984 [JP] Japan .................................. 59-28579

[51] Int. Cl.$^4$ .......................................... C07C 127/17
[52] U.S. Cl. ......................................... 564/56; 71/119
[58] Field of Search ........................................ 564/56

[56] References Cited

U.S. PATENT DOCUMENTS 4,143,061  3/1979  Kubo et al. ........................ 564/48
4,465,509  8/1984  Takematsu et al. ............... 564/56

Primary Examiner—Charles F. Warren
Assistant Examiner—Roberta A. Picard
Attorney, Agent, or Firm—Frishauf, Holtz, Goodman & Woodward

[57] ABSTRACT

Substituted 1,3-dibenzylureas are represented by the following general formula:

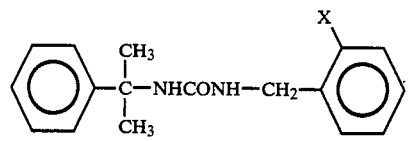

wherein X is a chlorine atom, a bromine atom, an iodine atom, a trifluoromethyl group, a methyl group or a methoxy group. These compounds are used as a herbicidal composition comprising at least one of said compounds and a carrier, if desired, together with a suitable adjuvant.

14 Claims, No Drawings

SUBSTITUTED 1,3-DIBENZYLUREAS AND HERBICIDAL COMPOSITIONS CONTAINING THEM

BACKGROUND OF THE INVENTION

1. Field of the Invention

This invention relates to substituted 1,3-dibenzylureas and herbicidal compositions containing them as active ingredients for selective weed control in paddy rice.

2. Description of Prior Art

Some compounds having chemical structures similar to the compounds of the invention have been reported and are well known in the art. Some of the typical compounds are shown in Table 1.

TABLE 1

| Comp. No. | Chemical structure | Literature |
|---|---|---|
| A | $\phi\text{-C}(CH_3)_2\text{-NHCONH-CH}_2\text{-}\phi$ | U.S. Pat. No. 4,039,577 Japan 53-41664 (Patent Publication) |
| B | $\phi\text{-C}(CH_3)_2\text{-NHCONH-CH}(CH_3)\text{-}\phi$ | U.S. Pat. No. 4,039,577 Japan 53-41664 (Patent Publication) |
| C | $\phi\text{-C}(CH_3)_2\text{-NHCONH-C}(CH_3)_2\text{-}\phi$ | U.S. Pat. No. 4,039,577 Japan 53-41664 (Patent Publication) |
| D | $(2\text{-Cl-}\phi)\text{-C}(CH_3)_2\text{-NHCONH-CH}_2\text{-}(\phi\text{-Cl})$ | Japan 52-83432 (Patent Public Disclosure) |
| E | $(2\text{-Cl-}\phi)\text{-C}(CH_3)_2\text{-NHCONH-CH}_2\text{-}\phi\text{-Cl}$ | Japan 52-83432 (Patent Public Disclosure) |

The compounds A to E shown in Table 1 are well known for herbicidal or other agricultural use. According to our experiments, as shown in some of the results of the examples presented hereinafter, the compounds A to E control undesirable weeds only to minor extents.

SUMMARY OF THE INVENTION

It is an object of the invention to provide novel substituted 1,3-dibenzylureas.

It is another object of the invention to provide a herbicidal composition which comprises a herbicidal amount of at least one of the substituted 1,3-dibenzylureas and a carrier material, if desired, together with a suitable adjuvant.

Other objects and advantages of this invention will become apparent to those skilled in the art by reference to the detailed description of the invention.

DETAILED DESCRIPTION OF THE PREFERRED EMBODIMENT

The compounds of this invention have the following general formula I:

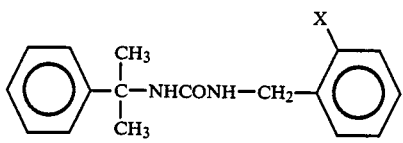

wherein X is a chlorine atom, a bromine atom, an iodine atom, a trifluoromethyl group, a methyl group or a methoxy group.

The compounds of formula I can be prepared, for example, by the following method: reacting an amine compound of formula II,

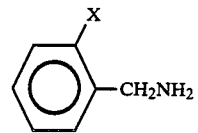

wherein X is as defined above with an isocyanate compound of formula III,

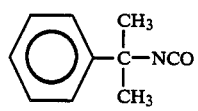

These reactions are carried out without any solvents or in the presence of inert organic solvents such as benzene, toluene, xylene, acetone, tetrahydrofuran, 1,4-dioxane, dichloromethane, chloroform, tetrachloromethane, pyridine, N,N-dimethylformamide, methanol and ethanol, water or mixtures of water with the above organic solvents. The reactions are carried out at from room temperature to 50° C. for from one to five hours with or without basic catalysts. The product contained in the reaction mixture can be separated and purified by conventional means such as recrystallization, distillation, adsorption, absorption, extractive distillation and any suitable combination of these.

The compounds of this invention embraced by formula I are as follows:

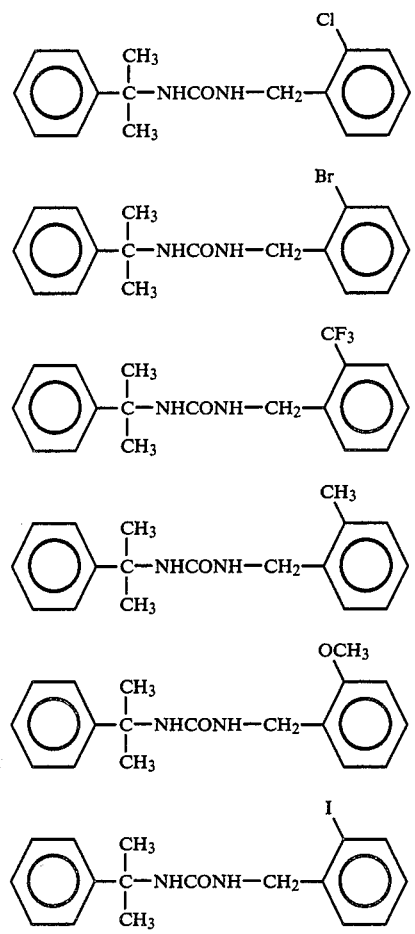

The above compound Nos. are used throughout in this specification.

The following illustrates one example of preparing the compounds of this invention.

Preparation of
1-(2-chlorobenzyl)-3-(α,α-dimethylbenzyl) urea (Comp. No. 1)

A mixture consisting of 18.1 g of α,α-dimethylbenzyl-isocyanate and 14.2 g of 2-chlorobenzylamine was allowed to stand for 2 hours at room temperature. The white deposit formed was then filtered off. Washing with n-hexane and recrystallization from ethanol gave 28.5 g of colorless crystal product, m.p. 165°–166° C.

The molecular structure of the product was confirmed by $^1$H NMR, the data of which are shown in Table 2.

Compound Nos. 2–6 were prepared by the same method as described above, the physical data of which are shown in Table 2 below.

TABLE 2

| Comp. No. | Melting point (°C.) | $^1$H NMR (60 MHz) |
|---|---|---|
| 1 | 165–166 | 1.55(6H,s), 4.21(2H,d), |

TABLE 2-continued

| Comp. No. | Melting point (°C.) | $^1$H NMR (60 MHz) |
|---|---|---|
|   |   | 6.19(1H,t,J=6Hz), 6.34(1H,s), 6.9–7.5(9H,m) |
| 2 | 181–183 | 1.56(6H,s), 4.18(2H,d,J=6Hz), 6.2(1H,t,J-6Hz), 6.35(1H,s), 6.8–7.5(9H,m) |
| 3 | 177–178 | 1.56(6H,s), 4.3(2H,d,J=6Hz), 6.2(1H,t,J=6Hz), 6.37(1H,s), 7.0–7.8(9H,m) |
| 4 | 145–146 | 1.55(6H,s), 2.26(3H,s), 4.1(2H,d,J=5Hz), 6.0(1H,t,J=5Hz), 6.17(1H,s), 6.9–7.6,(9H,m) |
| 5 | 143–144 | 1.54(6H,s), 3.78(3H,s), 4.1(2H,d,J=6Hz), 6.0(1H,t,J=6Hz), 6.29(1H,s), 6.6–7.6(9H,m) |
| 6 | 179–183 | 1.56(6H,s), 4.09(2H,d,J=6Hz), 6.2(1H,t,J=6Hz), 6.37(1H,s), 6.7–7.8(9H,m) |

We found that the compounds of formula I have extremely high selective herbicidal activity in paddy fields compared with the compounds shown in Table 1, which are well known in the art.

The strength of the herbicidal activity of the compounds of formula I, for example, on inhibiting the growth of *Scirpus juncoides Roxb.* is about 7 to 125 times greater for the root, and about 6 to 20 times greater for the shoot, than that of compound A, and about 150 to 2600 times greater for the root, and about 140 to 500 times greater for the shoot, than that of compound D.

It is not obvious why the compounds of this invention have extremely high herbicidal activity compared with the compounds shown in Table 1. We guess that the steric shapes of the compounds of this invention having relatively bulky substituent groups at the ortho-position of benzyl group may become suited to act as a chemicals acceptor in the weeds.

The compounds of this invention have an unexpectedly high degree of selective activities on annual and perennial cyperaceous weeds such as *Cyperus difformis L., Scirpus juncoides Roxb.* and *Cyperus serotinus Rottb.* in paddy fields. An outstanding feature of the compounds of this invention is that they exert a strong herbicidal action on perennial cyperaceous weeds such as *Cyperus serotinus Rottb., Eleocharis kuroguwai Ohwi* and *Eleocharis acicularis Roem.* et. Schult. which are very difficult to be controlled with conventional herbicides and, on the other hand, they do not damage paddy rice plants by whatever cultivation method, for example direct sowing in flooded paddy fields, direct sowing in well-drained paddy fields or transplanting of seedlings.

The compounds of this invention, as described above, differ from the aforementioned similar compounds in having unexpected features such as being much more effective and selective in the control of perennial cyperaceous weeds, e.g., *Cyperus serotinus Rottb.* and *Eleocharis acicularis Roem.* et Schult. without inhibiting the growth of paddy rice. It is well known that selective weed control is a very important feature in herbicides.

The herbicidal composition of this invention, which is a much more effective and selective herbicide in paddy fields, as described above, comprises at least one compound embraced by formula I as an active ingredient, carriers and, if necessary, adjuvants.

The application method of the herbicidal composition is preferably soil surface treatment and soil incorporation treatment, and more preferably soil surface treatment.

The application rate of the herbicidal composition is preferably about 0.25–2.8 kg ai/ha, and more preferably about 0.7–2.1 kg ai/ha.

The application time of the herbicidal composition is preferably from pre-emergence of weeds to about the 15th day after sowing of rice plants or transplanting of seedlings, and more preferably from pre-emergence of weeds to about the 10th day after sowing of rice plants or transplanting of seedlings.

The herbicidal composition of this invention can be used not only in the form of pure chemicals, but, for practical uses as herbicides, and depending on the nature of the fields of application, in the form of mixtures with inert solid or liquid carriers and adjuvants used and commonly referred to in the art, prepared in the form of granules, fine granules, wettable powders, emulsifiable concentrates, water soluble concentrates, dusts, crude dusts and tablets.

Examples of solid carriers are mineral powders such as calcium carbonates, apatite, gypsum, silica gel, vermiculite, mica, diatomaceous earth, talc, pyrophyllite, acid clay, clay, kaolinite, montmorillonite, bentonite, zieclite and white carbon; plant powders such as crystalline cellulose and starch; and high molecular compounds such as poly(vinyl chloride) and petroleum resin. Examples of liquid carriers are alcohols such as methanol, etheralcohols such as ethyleneglycol monoethyl ether, nitriles such as acetonitrile, acid amides such as N,N-dimethylformamide, ethers such as 1,4-dioxane and tetrahydrofuran, esters such as ethyl acetate, ketones such as acetone, chlorinated hydrocarbons such as chloroform and tetrachloromethane, aromatic hydrocarbons such as toluene, xylene, benzene, methylnaphthalene and chlorobenzene, other organic solvents such as dimethyl sulfoxide and isophorone, water and mixtures of water with any of the above organic solvents. All of these carriers can be used alone or admixed with others.

Adjuvants such as wetting agents, dispersing agents, emulsifying agents, spreading agents, adhesive agents and forming agents can also be used as auxiliary substances in the above preparation. Examples of adjuvants are various kinds of surface active agents such as nonionic types (e.g., polyoxyethylene-alkylaryl ether and polyoxyethylene-octylphenyl ether), cationic types (e.g., alkyldimethylbenzyl-ammonium chloride and alkylpyridinium chloride), anionic types (e.g., sodium ligninesulfonate and dialkylsulfo-succinate) and amphoteric types (e.g., alkyldimethylbetaine and dodecylaminoethylglycine). Each of these surface active agents can be used alone or admixed with others.

The active ingredients, substituted 1,3-dibenzylureas of this invention should be included in such compositions in sufficient amount that they can exert a herbicidal effect. Usually from about 0.5 to 95% by weight of the active ingredients may be included in such formulations.

The herbicidal composition of this invention can also be used together with other pesticides such as other herbicides, insecticides, fungicides and plant growth regulators or agricultural materials such as fertilizers and soil conditioning agents by pre-mixing or simultaneous applications.

In order to illustrate the preparation of the herbicidal composition of this invention, the following examples are given. All parts are given by weight unless otherwise indicated.

EXAMPLE 1

Preparation of a wettable powder

Sixty parts of compound No. 3, 25 parts of diatomaceous earth, 10 parts of talc and 5 parts of sodium alkylbenzenesulfonate were mixed and pulverized to give a wettable powder.

EXAMPLE 2

Preparation of a granular composition

A mixture of 7 parts of compound No. 1, 63 parts of bentonite, 27 parts of talc and 3 parts of dialkylsulfosuccinate was mixed with water to make granules, which were then dried to give a granular composition.

EXAMPLE 3

Preparation of a granular composition

Five parts of compound No. 2, 60 parts of bentonite, 32 parts of clay and 3 parts of sodium alkylbenzensulfonate were mixed and a granular composition was given by the same method as Example 2.

The herbicidal activities of the compounds of this invention are more fully illustrated by the following examples.

EXAMPLE 4

Pot test on inhibiting activity

Five germinated seeds of *Scirpus juncoides Roxb.* were put into a vial with 3 cm i.d. containing 5 ml of each test emulsion which was made by diluting wettable powder of each test compound, prepared as in the above Example 1, resulting in an active ingredient concentration of from 0.001 to 1,000 ppm. Each vial was then kept in a growth chamber at 25° C., 4,000 lux. On the 14th day after treatment, the inhibiting activity on the growth was evaluated by measuring the length of each shoot and root, from which the $ED_{90}$ value was discovered. $ED_{90}$ represents the effective dose with which elongation of shoot or root was 90% inhibited as compared with the control. The results are given in the following Table 3, in which the data of $ED_{90}$ were for an average of 2 replications, respectively.

TABLE 3

| Comp. No.[1] | $ED_{90}$ (ppm) Shoot | Root |
|---|---|---|
| 1 | 2.5 | 0.046 |
| 2 | 2.1 | 0.032 |
| 3 | 4.8 | 0.13 |
| 4 | 7.2 | 0.55 |
| 5 | 6.2 | 0.45 |
| 6 | 2.8 | 0.057 |
| A | 44 | 4.0 |
| B | 55 | 8.2 |
| C | 41 | 7.1 |
| D | 1000< | 85 |
| E | 1000< | 97 |

[1]control compounds A, B, C, D and E described above.

EXAMPLE 5

Pot test under transplanting cultivation

Paddy field soil was charged into a Wagner pot of 1/5000 are and seeds of *Cyperus difformis L.* and *Scripus juncoides Roxb.* were sowed uniformly in the upper layer of the soil. Two young rice seedlings of the second leaf shape, two tubers of *Cyperus serotinus Rottb.* and rhizomes of *Eleocharis acicularis Roem.* et Schult. were then transplanted thereinto and the pot was then filled with water up to a depth of about 3 cm over the soil. On the 3rd day after the sowing and the transplanting, a wettable powder containing 60% of each test compound, prepared as in the above Example 1, was dispersed in water and applied by dripping on to the surface of water at a rate of 500, 250, 125 and 62.5 g ai/ha. The pot was placed in a greenhouse. On the 21st day after treatment, the average herbicidal effects on weeds and phytotoxicity to paddy rice plant were evaluated on a numerical scale of from 0 to 5 as defined in the following Table 4.

TABLE 4

| Scale | Herbicidal effect (percent damage) | Scale | Phytotoxicity to rice |
|---|---|---|---|
| 5 | 100 | X | Kill |
| 4 | 80 | +++ | Severe damage |
| 3 | 60 | ++ | Considerable damage |
| 2 | 40 | + | Moderate damage |
| 1 | 20 | ± | Slight damage |
| 0 | 0 | − | No damage |

The results are given in the following Table 5.

TABLE 5

| Comp.[1] No. | Dose (g ai/ha) | Phytotoxicity | Herbicidal effect[2] C.d. | S.j. | C.s. | E.a. |
|---|---|---|---|---|---|---|
| 1 | 500 | — | 5 | 5 | 5 | 5 |
|   | 250 | — | 5 | 5 | 5 | 5 |
|   | 125 | — | 5 | 5 | 5 | 5 |
|   | 62.5 | — | 5 | 5 | 4.5 | 5 |
| 2 | 500 | — | 5 | 5 | 5 | 5 |
|   | 250 | — | 5 | 5 | 5 | 5 |
|   | 125 | — | 5 | 5 | 5 | 5 |
|   | 62.5 | — | 5 | 5 | 4.5 | 5 |
| 3 | 500 | — | 5 | 5 | 5 | 5 |
|   | 250 | — | 5 | 5 | 5 | 5 |
|   | 125 | — | 5 | 5 | 5 | 5 |
|   | 62.5 | — | 4.5 | 4.5 | 4 | 4.5 |
| 4 | 500 | — | 5 | 5 | 5 | 5 |
|   | 250 | — | 5 | 5 | 5 | 5 |
|   | 125 | — | 4.5 | 4.5 | 4.5 | 5 |
|   | 62.5 | — | 4.5 | 4.5 | 4.5 | 4.5 |
| 5 | 500 | — | 5 | 5 | 5 | 5 |
|   | 250 | — | 5 | 5 | 5 | 5 |
|   | 125 | — | 4 | 4 | 4.5 | 4.5 |
|   | 62.5 | — | 4 | 4 | 4.5 | 4.5 |
| 6 | 500 | — | 5 | 5 | 5 | 5 |
|   | 250 | — | 5 | 5 | 5 | 5 |
|   | 125 | — | 5 | 5 | 5 | 5 |
|   | 62.5 | — | 5 | 5 | 4.5 | 5 |
| A | 500 | — | 2 | 3 | 3 | 3 |
|   | 250 | — | 2 | 2 | 0 | 1 |
|   | 125 | — | 1 | 1 | 0 | 0 |
|   | 62.5 | — | 1 | 1 | 0 | 0 |
| B | 500 | — | 3 | 2 | 0 | 1 |
|   | 250 | — | 3 | 1 | 0 | 0 |
|   | 125 | — | 2 | 0 | 0 | 0 |
|   | 62.5 | — | 0 | 0 | 0 | 0 |
| C | 500 | — | 3 | 4 | 2 | 3 |
|   | 250 | — | 3 | 3 | 2 | 2 |
|   | 125 | — | 2 | 1 | 2 | 2 |
|   | 62.5 | — | 0 | 0 | 0 | 0 |
| D | 500 | — | 1 | 1 | 1 | 1 |
|   | 250 | — | 0 | 0 | 0 | 0 |
|   | 125 | — | 0 | 0 | 0 | 0 |
|   | 62.5 | — | 0 | 0 | 0 | 0 |
| E | 500 | — | 0 | 1 | 0 | 0 |
|   | 250 | — | 0 | 1 | 0 | 0 |
|   | 125 | — | 0 | 0 | 0 | 0 |
|   | 62.5 | — | 0 | 0 | 0 | 0 |

TABLE 5-continued

| Comp.[1] No. | Dose (g ai/ha) | Phytotoxicity | Herbicidal effect[2] C.d. | S.j. | C.s. | E.a. |
|---|---|---|---|---|---|---|
| Control | nil | — | 0 | 0 | 0 | 0 |

[1]control compounds A, B, C, D and E described above.
[2]C.d: *Cyperus difformis* L., S.j.: *Scirpus juncoides* Roxb,
C.s.: *cyperus serotinus* Rottb.,
E.a.: *Eleocharis acicularis* Roem. et Schult.

EXAMPLE 6

Pot test under direct sowing cultivation

Paddy field soil was charged into a Wagner pot of 1/2000 are and germinated seeds of *Scirpus juncoides* Roxb. and rice (kind: Akinishiki) were sowed in the upper layer of the coil. Eight tubers of *Cyperus serotinus Rottb.* and rhizomes of *Eleocharis acicularis Roem.* et Schult. were then put in the soil and the pot was filled with water up to a depth of about 3 cm over the soil. On the next day, a granular composition containing 7% of each test compound, prepared as in the above Example 2, was applied on to the surface of water at a rate of 0.5, 1.0 and 2.0 kg ai/ha. On the 30th day after treatment, the average herbicidal effect on weeds and phytotoxicity to rice plant of each test compound were evaluated on the basis of the scale defined in Example 5. The results are given in the following Table 6.

TABLE 6

| Comp.[1] No. | Dose (kg ai/ha) | Phytotoxicity | Herbicidal effect S.j. | C.s. | E.a. |
|---|---|---|---|---|---|
| 1 | 2 | — | 5 | 5 | 5 |
|   | 1 | — | 5 | 5 | 5 |
|   | 0.5 | — | 5 | 5 | 5 |
| 2 | 2 | — | 5 | 5 | 5 |
|   | 1 | — | 5 | 5 | 5 |
|   | 0.5 | — | 5 | 5 | 5 |
| 3 | 2 | — | 5 | 5 | 5 |
|   | 1 | — | 5 | 5 | 5 |
|   | 0.5 | — | 5 | 5 | 5 |
| 4 | 2 | — | 5 | 5 | 5 |
|   | 1 | — | 5 | 5 | 5 |
|   | 0.5 | — | 5 | 4.5 | 5 |
| 5 | 2 | — | 5 | 5 | 5 |
|   | 1 | — | 5 | 5 | 5 |
|   | 0.5 | — | 4.5 | 4 | 4.5 |
| 6 | 2 | — | 5 | 5 | 5 |
|   | 1 | — | 5 | 5 | 5 |
|   | 0.5 | — | 5 | 5 | 5 |
| A | 2 | — | 3 | 1 | 2 |
|   | 1 | — | 2 | 1 | 2 |
|   | 0.5 | — | 1 | 0 | 0 |
| B | 2 | — | 4 | 4 | 3 |
|   | 1 | — | 1 | 1 | 1 |
|   | 0.5 | — | 1 | 0 | 0 |
| C | 2 | — | 4 | 2 | 4 |
|   | 1 | — | 2 | 2 | 3 |
|   | 0.5 | — | 1 | 1 | 1 |
| D | 2 | — | 1 | 0 | 0 |
|   | 1 | — | 0 | 0 | 0 |
|   | 0.5 | — | 0 | 0 | 0 |
| E | 2 | — | 0 | 0 | 0 |
|   | 1 | — | 0 | 0 | 0 |
|   | 0.5 | — | 0 | 0 | 0. |
| Control | nil | — | 0 | 0 | 0 |

[1]control compounds A, B, C, D and E described above.
[2]S.j.: *Scirpus juncoides* Roxb.,
C.s.: *Cyperus serotinus* Rottb.,
E.a.: *Eleocharis acicularis* Roem. et Schult.

EXAMPLE 7

Paddy field test

A field test over an area of 2 m² was conducted in a manner similar to the pot test. On the 3rd day and the 10th day after transplanting and direct sowing of rice plants (kind: Akinishiki), a granular composition containing 7% of each test compound, prepared as in the above Example 2, was applied on to the surface of water at a rate of 0.7, 1.4 and 2.1 kg ai/ha. On the 30th day after treatment, the herbicidal effect and phytotoxicity were evaluated on the basis of the scale defined in Example 5. The results are given in the following Table 7.

TABLE 7

| Comp.[1] No | Application time[2] | Dose (kg ai/ha) | Phytotoxicity[3] r.d. | r.t. | Herbicidal effect[4] C.d. | S.j. | C.s. |
|---|---|---|---|---|---|---|---|
| 1 | 3rd day | 2.1 | — | — | 5 | 5 | 5 |
|   |         | 1.4 | — | — | 5 | 5 | 5 |
|   |         | 0.7 | — | — | 5 | 5 | 5 |
|   | 10th day| 2.1 | — | — | 5 | 5 | 5 |
|   |         | 1.4 | — | — | 5 | 5 | 5 |
|   |         | 0.7 | — | — | 5 | 5 | 5 |
| 2 | 3rd day | 2.1 | — | — | 5 | 5 | 5 |
|   |         | 1.4 | — | — | 5 | 5 | 5 |
|   |         | 0.7 | — | — | 5 | 5 | 5 |
|   | 10th day| 2.1 | — | — | 5 | 5 | 5 |
|   |         | 1.4 | — | — | 5 | 5 | 5 |
|   |         | 0.7 | — | — | 5 | 5 | 5 |
| A | 3rd day | 2.1 | — | — | 2 | 1 | 1 |
|   |         | 1.4 | — | — | 1 | 0 | 0 |
|   |         | 0.7 | — | — | 0 | 0 | 0 |
|   | 10th day| 2.1 | — | — | 1 | 1 | 1 |
|   |         | 1.4 | — | — | 1 | 1 | 0 |
|   |         | 0.7 | — | — | 0 | 0 | 0 |
| C | 3rd day | 2.1 | ± | — | 3 | 3 | 0 |
|   |         | 1.4 | — | — | 1 | 1 | 0 |
|   |         | 0.7 | — | — | 1 | 0 | 0 |
|   | 10th day| 2.1 | — | — | 3 | 1 | 0 |
|   |         | 1.4 | — | — | 0 | 1 | 0 |
|   |         | 0.7 | — | — | 0 | 0 | 0 |
| Control |   | nil | — | — | 0 | 0 | 0 |

[1] control compounds A and C described above
[2] the day after sowing and transplanting
[3] r.d.: rice plant under direct sowing cultivation
  r.t.: rice plant under transplanting cultivation
[4] C.d.: *Cyperus difformis* L., S.j.: *Scirpus juncoides* Roxb., C.s.: *Cyperus serotinus* Rottb.

What is claimed is:

1. A compound of the formula

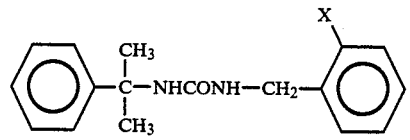

wherein X is selected from the group consisting of a chlorine atom, a bromine atom, an iodine atom, a trifluoromethyl group, a methyl group and a methoxy group.

2. The compound of claim 1, wherein X is a chlorine atom.

3. The compound of claim 1, wherein X is a bromine atom.

4. The compound of claim 1, wherein X is an iodine atom.

5. The compound of claim 1, wherein X is a trifluoromethyl group.

6. The compound of claim 1, wherein X is a methyl group.

7. The compound of claim 1, wherein X is a methoxy group.

8. A herbicidal composition which comprises a carrier, an adjuvant and an effective amount of a compound according to claim 1 as the herbicidally active ingredient.

9. A herbicidal composition which comprises a carrier, an adjuvant and an effective amount of a compound according to claim 2 as the herbicidally active ingredient.

10. A herbidical composition which comprises a carrier, an adjuvant and an effective amount of a compound according to claim 3 as the herbicidally active ingredient.

11. A herbicidal composition which comprises a carrier, an adjuvant and an effective amount of a compound according to claim 4 as the herbicidally active ingredient.

12. A herbicidal composition which comprises a carrier, an adjuvant and an effective amount of a compound according to claim 5 as the herbicidally active ingredient.

13. A herbicidal composition which comprises a carrier, an adjuvant and an effective amount of a compound according to claim 6 as the herbicidally active ingredient.

14. A herbicidal composition which comprises a carrier, an adjuvant and an effective amount of a compound according to claim 7 as the herbicidally active ingredient.

* * * * *